United States Patent [19]

Sans

[11] Patent Number: 5,045,052
[45] Date of Patent: Sep. 3, 1991

[54] SEALING DEVICE FOR CONTROLLING ILEO-COLOSTOMIES

[76] Inventor: José V. Sans, Burdeos, 8-10, 08029-Barcelona, Spain

[21] Appl. No.: 437,364

[22] Filed: Nov. 15, 1989

[30] Foreign Application Priority Data

Nov. 15, 1988 [ES] Spain ............................ 8803463
Oct. 25, 1989 [ES] Spain ............................ 903591

[51] Int. Cl.$^5$ ............................ A61F 2/02; A61F 5/44
[52] U.S. Cl. ............................ 600/32; 604/337
[58] Field of Search ............... 600/32; 604/337, 327, 604/328, 332

[56] References Cited

U.S. PATENT DOCUMENTS 2,243,529  5/1941  Grossman et al. ............... 600/32
4,351,322  9/1982  Prager ............................ 600/32

FOREIGN PATENT DOCUMENTS 2747245  4/1979  Fed. Rep. of Germany ........ 600/32
87/01274  3/1987  PCT Int'l Appl. ................ 600/32
0676293  7/1952  United Kingdom ................ 600/32

Primary Examiner—Randall L. Green
Assistant Examiner—R. Clarke
Attorney, Agent, or Firm—Michael J. Striker

[57] ABSTRACT

A sealing device for controlling ileo-colostomies comprises an external cover, a hollow stopper insertable into a hole or preternatural anus practiced, a base plate to be applied on an external face of an abdominal area and surrounding the hole or preternatural anus, and elements for releasably connecting the cover with the stopper and with the base plate.

18 Claims, 3 Drawing Sheets

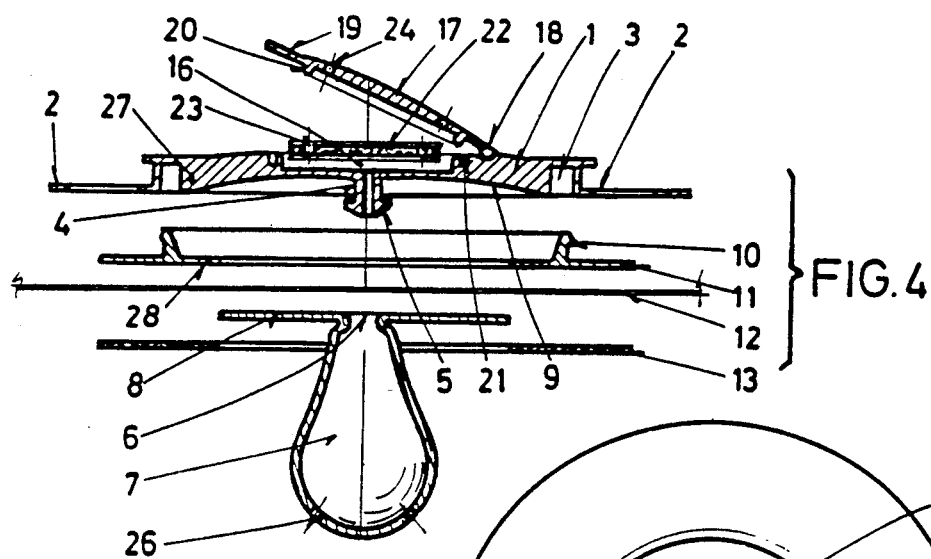
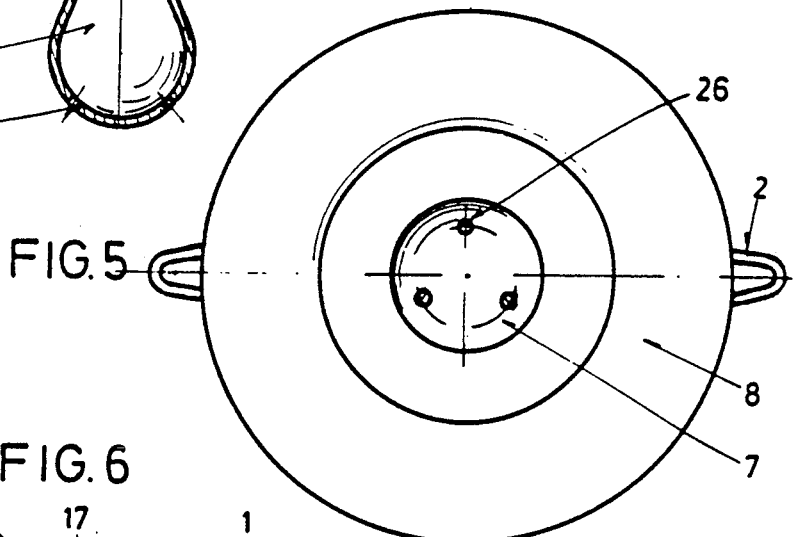
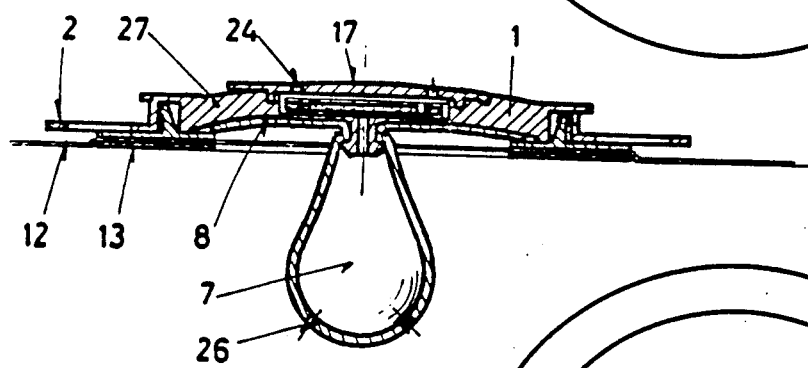
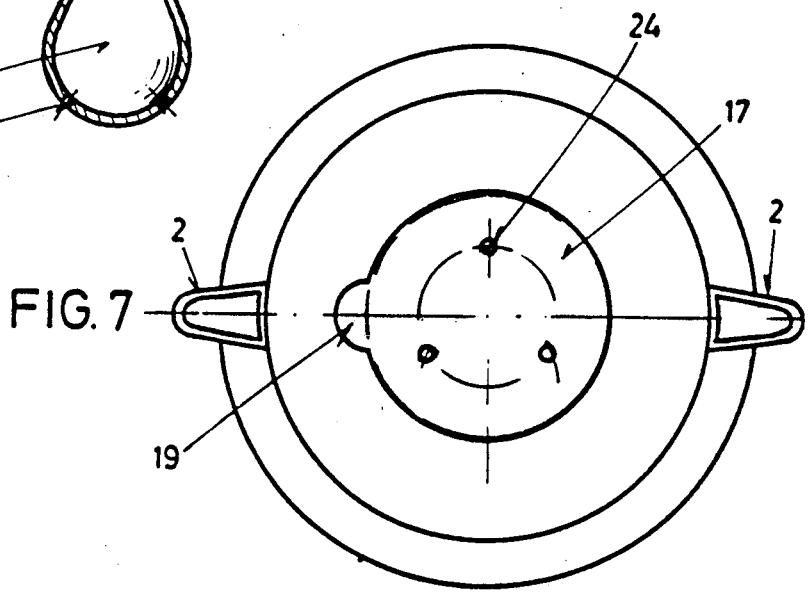

27
SEALING DEVICE FOR CONTROLLING ILEO-COLOSTOMIES

BACKGROUND OF THE INVENTION

The present invention relates to a sealing device for controlling ileo-colostomies. More particularly, it relates to such a sealing device that can be used by a patient in a practical and easy way to reduce personal difficulties or in other words to live with an ostomy and reduce the difficulties related to dieting, medications, sexual practices, personal hygiene and certain social problems.

Sealing devices of the above mentioned general type are known in the art. Known devices are adopted by many operated persons to whom a preternatural anus was practised. A known device includes a ring which is secured on the external abdominal wall and to which a bag collecting the evacuations (colostomy bag) is applied and locked. The known technology improved this approach by withdrawing the bag when it is not required and using instead a closing stopper-like element which is introduced in the colon opening and secured to the respective area. The securing is performed either magnetically, such as for example in a closure model developed by H. Feustel and G. Henning and presented at the Congress of Surgery of Munich in 1975. The securing can also be performed simply by pressure and an expansive sealing device in accordance with the model developed in 1986 by Flemming Burcharth, Frederik Kylberg, Akell Ballan and Sten Norby Rasmussen of the Department of Surgical Gastroenterology of Denmark, Department of Surgery, Sweden and Department of Medical Gastroenterology, Denmark.

The above listed constructions possess however several drawbacks. The first device must be sewn on the abdominal wall and the magnetic ring which cooperates with a magnet must be lodged inside a stopper. Another magnetic ring is also required for surrounding the central magnet. The insertion of the ring to be located around the preternatural anus means a surgical operation that is not free of further drawbacks, such as irritations, abcesses and remaining disturbances associated with this type of implantation.

In the device in accordance with the second construction, two parts are involved, one formed by an adhesive plate applicable to the abdominal wall, and another by a dispensable seal pressed on such plate. A seal is composed of soft flexible plastic material and contains a carbon filter packed in a water-soluble film that disintegrates and allows expansion of the seal to prevent the passage of the feces. This construction is complicated, troublesome and susceptible to difficulties in certain patients.

SUMMARY OF THE INVENTION

Accordingly, it is an object of the present invention to provide a sealing device for controlling ileo-colostomies which avoids the disadvantages of the prior art.

In keeping with these objects and with others which will become apparent hereinafter, one feature of the present invention resides, briefly stated, in a sealing device for controlling ileo-colostomies which has an external cover, a sealing stopper connectable with the cover and a base plate which can include a sheet of a porous adhesive and a washer in Karaya. Also a retaining ring for the cover can be provided. When the sealing device is designed in accordance with the present invention, it is composed of elements which are easy to fit and free of defects of the known constructions.

In accordance with another feature of the present invention the cover can be provided with a rim which is engageable with the stopper to couple the former with the latter.

Still a further feature of the present invention is that the base plate and the cover can be provided with coupling means formed, for example as cooperating projection and groove.

The cover can be composed of hard material such as a synthetic plastic material, while the stopper can be composed of an elastic material, such as for example rubber.

In accordance with a further advantageous feature of the present invention means are provided for suppressing bad smell of exhaust gases or winds from the patient.

The bad smell suppressing means can include a plurality of holes formed in a wall of the hollow stopper, a central passage formed in a rim which couples the cover with the stopper, holes formed in a bad smell suppressing element which is accommodated in the cover, and holes formed in a hinged additional cover part. As a result, the gases or winds pass through the holes of the stopper into its interior and then through the central passage of the rim into an enclosure incorporating the bad smell suppressing element, and then are discharged through the holes of the additional cover.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4 is a view showing a section of a sealing device in accordance with a second embodiment of the present invention;

FIG. 5 is a view showing the inventive sealing device of FIG. 4 from below;

FIG. 6 is a view showing the sealing device of FIG. 4 in an assembled condition;

FIG. 7 is a view showing the sealing device of FIG. 4 from above;

DESCRIPTION OF THE PREFERRED EMBODIMENTS

Figure 1:
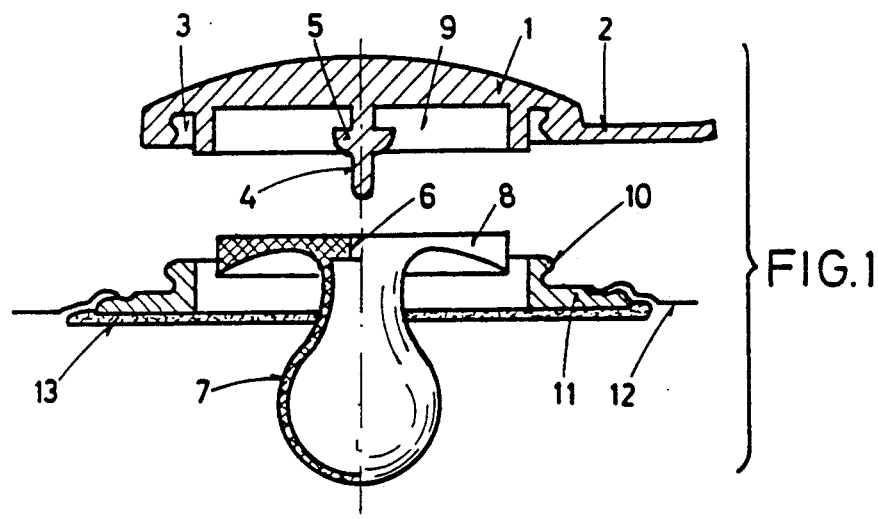
FIG. 1 is a view showing a section of the sealing device for controlling ileo-colostomies in accordance with a first embodiment of the present invention.
Figure 2:
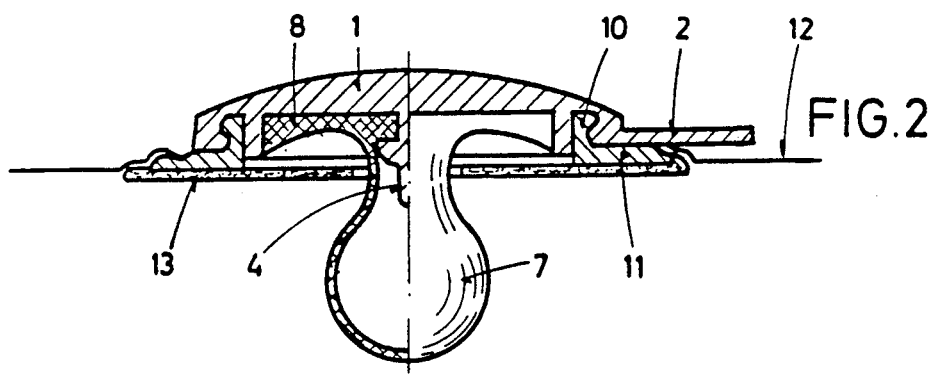
FIG. 2 is a view substantially corresponding to the view of FIG. 1, but showing the parts of the sealing device in an assembled condition.
Figure 3:
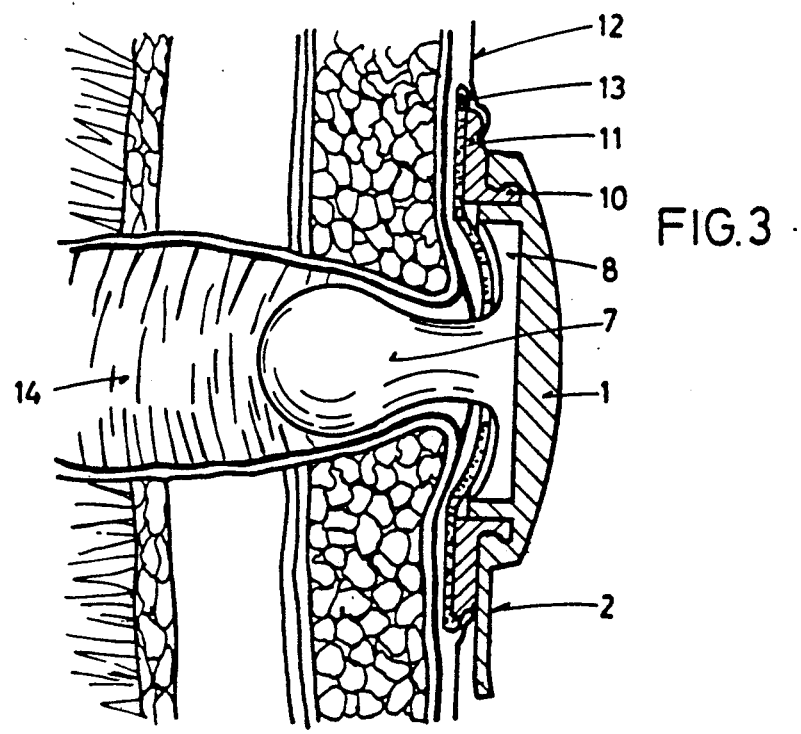
FIG. 3 is a view showing the inventive sealing device applied to the patient.

A sealing device in accordance with the present invention is shown in FIGS. 1–3. It has a circular cover which is identified with reference numeral 1 and slightly dished. The cover is composed of a plastic material and provided with a side flange 2. It further has an annular coupling recess 3 and an internal stem or tongue 4 provided with a hooking rim 5. A hollow sealing stopper 7 has a throttled neck 6 in which the hooking rim 5 is introduced and secured by pressure. The stopper 7 is substantially pear-shaped and has a collar 8 which is formed to be inserted into a ceiling or recess 9 which surrounds the stem 4. The stopper can be made of rubber or the like. When it is coupled to the cover 1, it forms an assembly shown in FIG. 2. The assembly is additionally secured by pressure and forced insertion of an edge 10 of the plug 7 into the annular recess 3. The annular recess 3 forms a female element, while the edge 10 forms a male element and provided on an annular portion 11 of the plug 7. A sheet of porous adhesive 12 and a Karaya rubber washer 13 which form a bottom base of the assembly are sticked to the annular portion 11.

FIG. 3 shows how the inventive device is applied and how the sealing stopper 7 penetrates in a colon hole 14, passing through a communication opening also called preternatural anus practiced in it. The two components namely the cover 1 and the stopper 7 are made solid due to the central hooking system formed by the stem 4 and the hole 6. The assembly of these two components can be pressed to the ring 11, by cooperation of the male ring edge 10 with the female annular recess 3 as shown in FIG. 2. In the closing phase shown in FIG. 3, the sealing is complete for the feces and gases. When opening is required for evacuation, it is sufficient to withdraw the stopper through the rim 2 and to release the anus hole for cotting, also pressed, the proper colostomy bag.

When the device is designed in accordance with the present invention as shown in FIGS. 1-3, it has many advantages. It is not necessary to undertake surgical operation in the abdominal wall to occlude any foreign body, for example, a magnet of one of the models on the market. All the parts used are resistant to natural liquids, and the sealing device is fit for any diameter of the anus hole due to its elasticity. In addition, the stopper with the shape of a pear has the advantage to contribute to retaining, apart from securing by means of the external coupling 3-10. The assembly can be perfectly thoroughly cleaned, after taking it apart by simple unhooking of the components 1 and 7. When the sealing device is taken apart, the ring of the usual colostomy bag can be fit to the ring 11 to receive the feces when fit. The device is very easy to fit, has a long life and a low cost.

The inventive device in accordance with a further embodiment of the present invention is shown in FIGS. 4-9. The device also includes a cover or main circular lid 1' composed of a plastic material and provided with two side handling rims 2' and an annular channel 3'. The cover 1' has a dished recess 9 and a central stem 4' provided with an end rim 5' and a hole 15. The hole 15 communicates with a circular enclosure 16 closed by an auxiliary lid 17. The lid 17 is hinged at a point 18 and provided with a handling rim 19 and a male rib 20. The rib 20 is engageable in a female necking 21 to insure a pressed closing of the enclosure 16. A disc-shaped tablet of activated carbon 22 possessing holes 23 is received in the enclosure 16. The lid 17 is also perforated by several holes 24 shown in FIG. 8, that communicate the enclosure 16 with outside. The thickness of the tablet 22 is selected so that a small chamber 25 remains between the tablet and a sealing of the lid 17.

Figure 8:
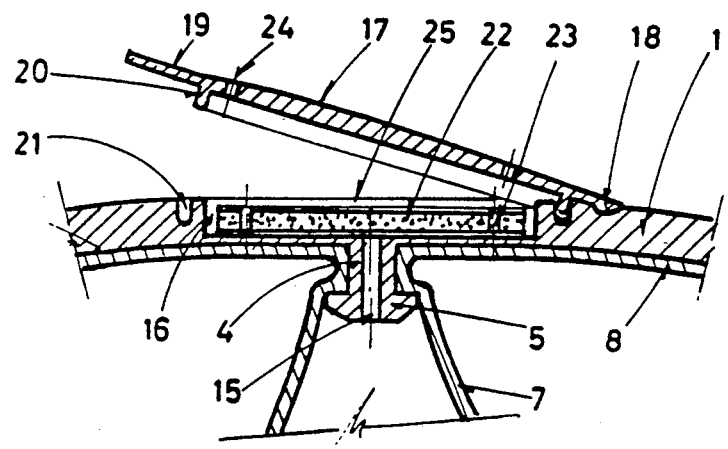
FIG. 8 is a view showing a fragment of the sealing device of FIG. 4 with a smell suppressing means, on an enlarged scale.

A hollow pear-shaped stopper 7' has an elastic collar 8' insertable into the dished recess 9'. In addition, it is provided with a throttled mouth 6' which is pressed hooked with the stem 4' as shown in FIG. 8. The stopper 7 has several holes 26. After the coupling is achieved, the two components 1' and 7' form an assembly such that the stopper 7' follows the cover 1' as much when the preternatural anus presses in the colon 14 is opened as when it is closed.

Figure 9:
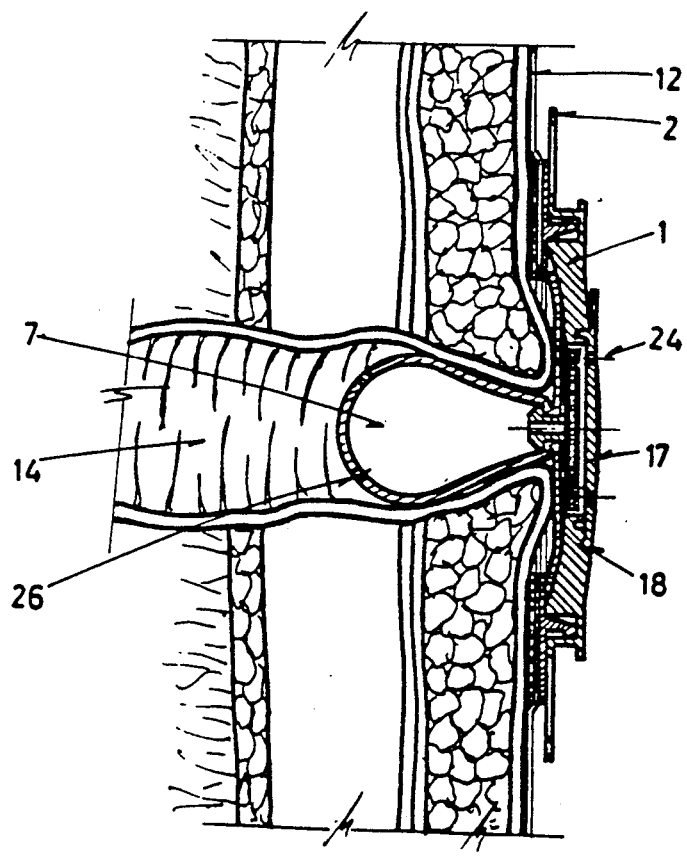
FIG. 9 is a view showing the sealing device of FIG. 4 applied to a patient.

The device of this embodiment is completed with the ring 11' which has a profiled annular rib 10' acting as a male hooking element which forcedly penetrates in the channel 3'. In this setting position, an internal edge 27 of the cover 1' comes to impinge on an internal rim 28 of the ring 11' forming there a tight closing line. The external face of the ring 11' receives an adhesive sheet 12', to which a flat washer 13' is secured. The washer 13' has an outside face provided with adhesive. The elements 12' and 13' ensure the adherence of the assembly on the epidermis of the area surrounding the hole practiced in the colon 14 as shown in FIG. 9.

The device in accordance with this embodiment has the following advantages. The cover 1' has a hooking stem 4' which is axially drilled to allow the passage of the gases (winds) toward the enclosure 16, where they lose their smell during crossing through the activated carbon tablet 22. The outlet to outside is guaranted by the holes 23 of the tablet and the holes 24 of the lid 17. The hinged lid 17 allows the easy replacement of the tablet of activated carbon 22, which gives passage to the gases that, before going outside, slow down in the chamber 25 for a good contact with the carbon to lose the bad smell. The inside of the stopper 7' communicates with the enclosure 16 through the passageway 15 so that the gases coming from the intestine 14 unavoidably go outside passing through the tablet 22 and the lid 17. The sealing or closing stopper 7' has several holes 26 for the flow of the gases, and the holes in a variable number are practiced in a line or level that can never be obstructed by the wall of the intestine 14. The number of holes of the lid 17, of the tablet 22, and the stopper 7' is variable, but it is never less than two for securing that at least one of them is uncovered for freely expelling the gases. The anus can be closed with the above described device as well as with a usual colostomy bag, as required by the user. During the day the device is normally used, while during the night as the excretion cannot be controlled, the above mentioned bag is permanently applied to collect the feces and the gases. The components 1' and 11' are of a semi-hard nature for example composed of proper plastic material. The parts 7', 12' and 13' are soft, for example flexible or elastic. The former is produced of an appropriate elastomer, such as natural or synthetic rubber. The sheet 12' is of a porous adhesive paper, and the washer 13' is composed of a usual Karaya rubber.

It should be noted that the internal diameter of the washer 13' that up to now was hand cut according to the surface of the area occupied by the hole of the anus, is now factory set so that no handling is required since the device is delivered in several sizes. This provides for several advantages both for the patient and for the medical personnel.

The way the above described device operates is believed to be clear. With this device the closure is perfect, the handling offers no difficulties, the patient can use the sealing device during the day being secured that the gases (winds) that can be produced will go out without any unpleasant smell, while during the night (or also during the day if required) he can replace it by a normal feces collecting bag, the simplicity of closing and opening ensures a total hygiene of the area operated and the materials used in the stopper cause no trouble due to their softness.

The materials, shapes and sizes of different components of the inventive device can be varied.

It will be understood that each of the elements described above, or two or more together, may also find a useful application in other types of constructions differing from the types described above.

While the invention has been illustrated and described as embodied in a sealing for controlling ileocolostomies, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A sealing device for controlling ileo-colostomies, comprising an external cover; a hollow stopper insertable into a hole or preternatural anus practiced; a base plate to be applied on an external face of an abdominal area and surrounding the hole or preternatural anus; and means for detachably connecting said cover with said stopper and with said base plate and including connecting formations provided on said stopper and said cover and detachably engageable with one another, so that said stopper can be connected with said cover by pressing said stopper against said cover, and said stopper can be withdrawn from said cover being replaced by a colostomy bag or another stopper.

2. A sealing device as defined in claim 1, wherein said stopper is formed as an elastic hollow stopper.

3. A sealing device as defined in claim 1, wherein said cover has a rim arranged to be coupled with said stopper.

4. A sealing device as defined in claim 1, wherein said base plate includes a porous adhesive and a Karaya washer.

5. A sealing device as defined in claim 1, wherein said cover is composed of a hard material, while said stopper is composed of a soft material.

6. A sealing device for controlling ileo-colostomies, comprising an external cover; a hollow stopper insertable into a hole or preternatural anus practiced; a base plate to be applied on an external face of an abdominal area and surrounding the hole or preternatural anus; and means for releasably connecting said cover with said stopper and with said base plate, said cover being provided with a stem having a hooking edge, said stopper being provided with a hole in which said stem engages to detachably connect said cover with said stopper.

7. A sealing device as defined in claim 6, wherein said cover has an annular recess surrounding a stem, said stopper having a collar insertable into said recess.

8. A sealing device as defined in claim 1, wherein said cover has a female annular recess, said base plate having a male edge engaged in said annular recess so that by pulling said cover said stopper can be withdrawn from the hole or preternatural anus to allow application of a colostomy bag.

9. A sealing device as defined in claim 1; and further comprising exhaust means for discharging gases or winds.

10. A sealing device for controlling ileo-colostomies, comprising an external cover; a hollow stopper insertable into a hole or preternatural anus practiced; a base plate to be applied on an external face of a an abdominal area and surrounding the hole or preternatural anus; and means for releasably connecting said cover with said stopper and with said base plate; and exhaust means for discharging gases or winds, said exhaust means including a hollow formed in said stopper and a plurality of holes also formed in said stopper and communicating said hollow with outside, a central stem connecting said cover with said stopper and provided with a central passing hole, and an enclosure formed in said cover and accommodating a bad smell suppressing element, so that gases or winds from an interior of intestine flow through said holes in said stopper into said hollow and then through said passing hole in said central stem into said enclosure and through said bad smell suppressing element.

11. A sealing device as defined in claim 10, wherein said cover includes a main lid and an additional lid, said enclosure being formed in said main lid.

12. A sealing device as defined in claim 10, wherein said bad smell suppressing element is formed as a tablet of activated carbon.

13. A sealing device as defined in claim 11, wherein said additional lid is hingedly connected with said main lid and closes said enclosure in its closed condition.

14. A sealing device as defined in claim 13; and further comprising means for coupling said additional lid with said main lid and including cooperating groove and projection provided on a respective one of said lids.

15. A sealing device as defined in claim 10, wherein said enclosure has a predetermined depth, said bad smell suppressing element having a thickness which is selected so that a chamber is formed between said bad smell suppressing element and said additional lid for slowing down the gases or winds.

16. A sealing device as defined in claim 11, wherein said bad smell suppressing element has a plurality of holes, said additional lid having a plurality of holes, said holes of each of said bad smell suppressing element, said additional lid and said stopper including at least two such holes.

17. A sealing device as defined in claim 10, wherein said holes of said stopper are arranged so that they cannot be obstructed by a wall of a colon when said stopper is introduced inside the latter.

18. A sealing device for controlling ileo-colostomies, comprising an external cover; a hollow stopper insertable into a hole or preternatural anus practiced; a base plate to be applied or an external face of an abdominal area and surrounding the hole or preternatural anus; and means for releasably connecting said cover with said stopper and with said base plate, said stopper having a collar, said base plate including a ring provided with an internal rim, said cover being applied to said collar of said stopper and having an annular edge abutting against said internal rim of said base plate, and defining a hole in the region of an area surrounding the anus opening.

* * * * *